(12) United States Patent
Morrison et al.

(10) Patent No.: US 6,214,300 B1
(45) Date of Patent: Apr. 10, 2001

(54) MICROENCAPSULATION AND ELECTROSTATIC PROCESSING DEVICE

(75) Inventors: Dennis R. Morrison, Kemah; Benjamin Mosier, Houston, both of TX (US); John M. Cassanto, Downingtown, PA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/079,833

(22) Filed: May 15, 1998

Related U.S. Application Data

(63) Continuation-in-part of application No. 08/349,169, filed on Dec. 2, 1994, now Pat. No. 5,827,531.

(51) Int. Cl.$^7$ ..................................................... B01J 13/06
(52) U.S. Cl. ........................ 422/238; 422/236; 422/131; 422/129; 210/416.1; 210/445
(58) Field of Search .................................. 422/237, 239, 422/236, 238, 256, 242, 134, 131, 129; 210/321.63, 321.75, 321.78, 416.1, 385, 634, 445, 637, 350, 351; 261/5, 6; 435/297.2, 297.1; 264/4, 4.1; 516/21, 53; 366/176.1–176.4, 267, 268

(56) References Cited

U.S. PATENT DOCUMENTS

Re. 34,828   1/1995   Sirkar ..................................... 210/137
191,131 *   5/1877   Gainey ................................... 210/350

(List continued on next page.)

Primary Examiner—Shrive Beck
Assistant Examiner—Susan Ohorodnik
(74) Attorney, Agent, or Firm—James M. Cate

(57) ABSTRACT

A microencapsulation and electrostatic processing (MEP) device is provided for forming microcapsules. In one embodiment, the device comprises a chamber having a filter which separates a first region in the chamber from a second region in the chamber. An aqueous solution is introduced into the first region through an inlet port, and a hydrocarbon/polymer solution is introduced into the second region through another inlet port. The filter acts to stabilize the interface and suppress mixing between the two immiscible solutions as they are being introduced into their respective regions. After the solutions have been introduced and have become quiescent, the interface is gently separated from the filter. At this point, spontaneous formation of microcapsules at the interface may begin to occur, or some fluid motion may be provided to induce microcapsule formation. In any case, the fluid shear force at the interface is limited to less than 100 dynes/cm$^2$. This low-shear approach to microcapsule formation yields microcapsules with good sphericity and desirable size distribution. The MEP device is also capable of downstream processing of microcapsules, including rinsing, re-suspension in tertiary fluids, electrostatic deposition of ancillary coatings, and free-fluid electrophoretic separation of charged microcapsules.

6 Claims, 13 Drawing Sheets

U.S. PATENT DOCUMENTS

| | | | |
|---|---|---|---|
| 4,110,529 | 8/1978 | Stoy | 528/491 |
| 4,201,691 | 5/1980 | Asher et al. | 252/314 |
| 4,229,297 | 10/1980 | Nohmi et al. | 210/654 |
| 4,274,956 | 6/1981 | Stewart | 210/638 |
| 4,822,491 | 4/1989 | Ostertag | 210/638 |
| 4,939,090 | 7/1990 | Taylor | 435/134 |
| 4,966,707 | 10/1990 | Cussler et al. | 210/632 |
| 4,971,688 * | 11/1990 | Francois et al. | 210/94 |
| 5,053,132 | 10/1991 | Sirkar | 210/500 |
| 5,135,740 | 8/1992 | Katz et al. | 424/401 |
| 5,185,108 | 2/1993 | Shimandle | 264/11 |
| 5,376,279 * | 12/1994 | Judd et al. | 210/681 |
| 5,376,347 * | 12/1994 | Ipponmatsu et al. | 423/338 |
| 5,457,986 | 10/1995 | DiLeo et al. | 73/38 |
| 5,478,478 | 12/1995 | Griswold | 210/745 |
| 5,480,547 | 1/1996 | Williamson et al. | 210/533 |
| 5,490,884 | 2/1996 | Robinson et al. | 95/45 |
| 5,510,068 | 4/1996 | Parmentier | 264/117 |
| 5,525,235 | 6/1996 | Chen et al. | 210/641 |
| 5,645,891 | 7/1997 | Liu et al. | 427/376.2 |
| 5,908,054 * | 7/1999 | Safabash et al. | 141/26 |
| 5,957,166 * | 9/1999 | Safabash | 141/26 |

* cited by examiner

|  | Group 1 | Group 2 |
|---|---|---|
| Forming Solution 1 | Solvent 1 is a hydrocarbon<br>Polymers are hydrocarbon soluble, selected to form the outer coating (typically of lower HLB values)<br>Co-solvents alcohols, hydrocarbons (act as co-surfactants)<br>Oils saturated or unsaturated oils<br>Drug dissolved (or suspended particulate) | Solvent 1 is aqueous<br>Polymers (skin) are water soluble, but can be extended into organic phase (includes phospholipids)<br>Co-solvents same, but often less %<br><br>Oils same<br>Drug dissolved (or particulate) |
| Forming Solution 2 | Solvent 2 aqueous<br>Polymers water soluble (PEG, Dextran)<br>Surfactants (typically higher HLB value)<br>Salts ionic, quaternary ammonium salts<br>Drugs aqueous soluble | Solvent 2 same<br>Polymers same<br>Surfactants same but often less %<br>Salts same, but often different %<br>Drugs aqueous soluble |
| Storage Solution | Oils hydrocarbons<br>Polymers hydrocarbon-soluble   -OR-<br>Drugs can be included | Alternative aqueous solution<br>polymers - aqueous soluble<br>coating-adjuvants immunoglobulins |
| Coating Solution | aqueous or hydrocarbon solution<br>coating- adjuvants, immunoglobulins, waxes, alginates, charged polymers, hydrocolloids, polysaccharides, polypeptides | |
| Electrophoretic Buffer | Low Conductivity solution, such as .0001 to .01 molar salt solution (typical conductivity <1.5x10$^{-3}$ mho/cm) | |

FIG. 1A

| Primary Solution | Secondary Solution |
|---|---|
| First Solvent (75-90%)<br>ethyl alcohol, methyl alcohol, isopropyl alcohol | Second Solvent (70-98%)<br>water |
| Organic Co-solvent 0-20%<br>$C_4$-$C_8$ alcohols (tetrahydrofuran (THF), dioxane, acetonitrile, dimethylformamide (DMF), dimethyl sulfoxide (DMSO)) | |
| Polymers (1-5%)<br>monoglycerated (glycerol monostearate, glycerol monooleate, glycerol monolaurate, mixtures of monoglycerates)<br><br>polyglycerides (glycerol dioleate, glycerol distearate)<br><br>sterols (cholesterol, plant sterols (e.g. stigmasterol, phytosterol, campesterol))<br><br>phospholipids (lecithins, e.g. phosphatydl choline aka Centrolex-F™) | Polymers (1-10%)<br>polyethylene glycol (PEG) - 400-20,000 daltons<br><br>polysaccharides (range 4000-100,000 daltons)<br><br>Others (Polyvinylpyrrolidone (PVP), polyvinyl alcohols, polyvinyl acetate)<br><br>Surfactants (HLB > ~15) (1-4%)<br>ionic and non-ionic (sorbitan monooleate with ethylene oxides, Dextran, PEG, $C_{12}$-$C_{20}$ fatty acid, quaternary $NH_4$, ethoxylated salts) |
| Water (1-10%)<br><br>Oils (1-10%)<br>unsaturated or saturated (iodinated poppy seed oil (IPO), mineral oil, cotton seed oil, olive oil, safflower oil, canola oil, peanut oil, sesame oil, corn oil) | Additional Polymers (1-10%)<br>hydrocolloids (gelatin, gum tragacanth, carrageenans, karaya gum, guar gum, alginates)<br><br>celluloses (CMC, HEC, HPC)<br><br>Salts (0.01-3%)<br>NaCl, KCl, $CaCl_2$, quaternary $NH_4$ salts, PPD, cetyl trimethylammonium bromide, 2M2A-AMP (ammonium ethyl propanol), Phosphate buffered saline (PBS) |
| Dissolved Drugs (1% to saturation) | Dissolved Drugs (1% to saturation)<br>therapeutic of choice |

FIG. 1B

| Primary Solution | Secondary Solution |
|---|---|
| First Solvent (70-90%) <br> water | First Solvent (75-90%) <br> ethyl alcohol, methyl alcohol, isopropyl alcohol |
| Co-solvents (0-20%) <br> $C_3$-$C_8$ alcohols (tetrahydrofuran (THF), dioxane, acetonitrile, dimethylformamide (DMF), dimethyl sulfoxide (DMSO)) | Co-Solvents <br> Same as primary solution |
| Polymers hydrophilic <br> water soluble polymers (polyvinylpyrrolidone (PVP), polyvinyl alcohols, polyvinyl acetate) <br><br> hydrocolloids (gelatin, gum tragacanth, gum arabic, gum accacia, carrageenans, karaya gum, guar gum) <br><br> alginates <br><br> celluloses (CMC, CPC, HEC) <br><br> phospholipids (lecithins, phosphatydl choline (Centrolex F)) <br><br> polysaccharides (corn starch, cyclodextrins) | Polymers (1-10%) <br> monoglycerated (glycerol monostearate, glycerol monooleate, glycerol monolaurate, mixtures of monoglycerates) <br><br> polyglycerides (glycerol dioleate, glycerol distearate) <br><br> sterols (cholesterol, plant sterols (e.g. stigmasterol, phytosterol, campesterol)) <br><br> phospholipids (lecithins, e.g. phosphatydl choline aka Centrolex F) <br><br> Surfactants (HLB > ~15) (1-4%) <br> ionic and non-ionic (sorbitan monooleate with ethylene oxides, Dextran, PEG, $C_{12}$-$C_{20}$ fatty acid, quaternary $NH_4$, ethoxylated salts) |
| Oils 1-10% <br> unsaturated or saturated (iodinated poppy seed oil (IPO), mineral oil, cotton seed oil, olive oil, safflower oil, canola oil, peanut oil, sesame oil, corn oil) | Additional Polymers 1-10% <br><br> Salts (0.01-3%) <br> NaCl, KCl, $CaCl_2$, quaternary $NH_4$ salts, cetyl trimethylammonium bromide, 2M2A-AMP (ammonium ethyl propanol), PPD, Phosphate buffered saline (PBS) |
| Dissolved Drugs <br> 1% to saturation | Dissolved Drugs <br> 1% to saturation |

FIG. 1C

| Coating/Wash Solution | Electrophoretic Solution | Storage Solution |
|---|---|---|
| hydrocarbon or aqueous solution | hydrocarbon solution | hydrocarbon solution |
| aqueous (water, polyethylene glycol, PVA, PVP, dextran, gelatin, gum arabic, guar gum) | aqueous solution<br>water<br><br>glycine, glucose, sorbitol<br><br>sucrose (0-8%)<br><br>ampholenes (0-1%)<br><br>ficoll 400,000 (0-20%)<br><br>NaCl, KCl (keep conductivity <1.5x10$^{-3}$ mho/cm) | oils (IPO, olive oil, heavy mineral oil, others which are same as in primary soln.)<br><br>paraffins ($C_{14}$-$C_{60}$)<br><br>Polymers (same as in secondary solution)<br><br>Add'l Polymers (same as secondary solution)<br><br>dissolved drugs (1% to saturation) |
| anionic coating materials<br>phosphatidyl serine    polyglutamic acid<br>beef heart cardiolipid    alkylsulfonate<br>polylactides    polylactic acid<br>polygalactides    dicetyl phosphate<br>serum proteins    serum peptides<br>bees wax    canuba wax<br>heparin-sodium    alginates<br>polyvinylpyrolidone    vancomycin<br>collagen    gelatin<br>succinyl-poly L-lysine<br>polyanion protamine sulfate<br>carboxymethylated chitosin<br>halogenated phosphatidyl choline<br>anionic surfactants (alykyl-sulfonate)<br>polyhydroxylmethylmethacrylate/polyamine | | |
| cationic coating materials<br>polyhistidine    polyarginine    chitosan<br>stearylamine    polylysine    lysine<br>protamine    trypsin    lysozyme<br>glycoproteins    cationic liposomes<br>cetylpyridium Cl    gelatin<br>polycation protamine sulfate | | aqueous solution<br>water<br><br>immunoglobulins, albumin, gelatin, hydrocolloids, plant sterols, phospholipids, polysaccharides (starches, cyclodextrins)<br><br>Polymers (same as in secondary solution)<br><br>Add'l Polymers (same as secondary solution)<br><br>dissolved drugs (1% to saturation) |
| zwitterion coating materials<br>phosphatidyl choline    amino butyric acid<br>cyclodextrins    amphoterics | | |
| Other coating materials<br>PEG 8000    fibronectin    ampholytes | | |

FIG. 1D

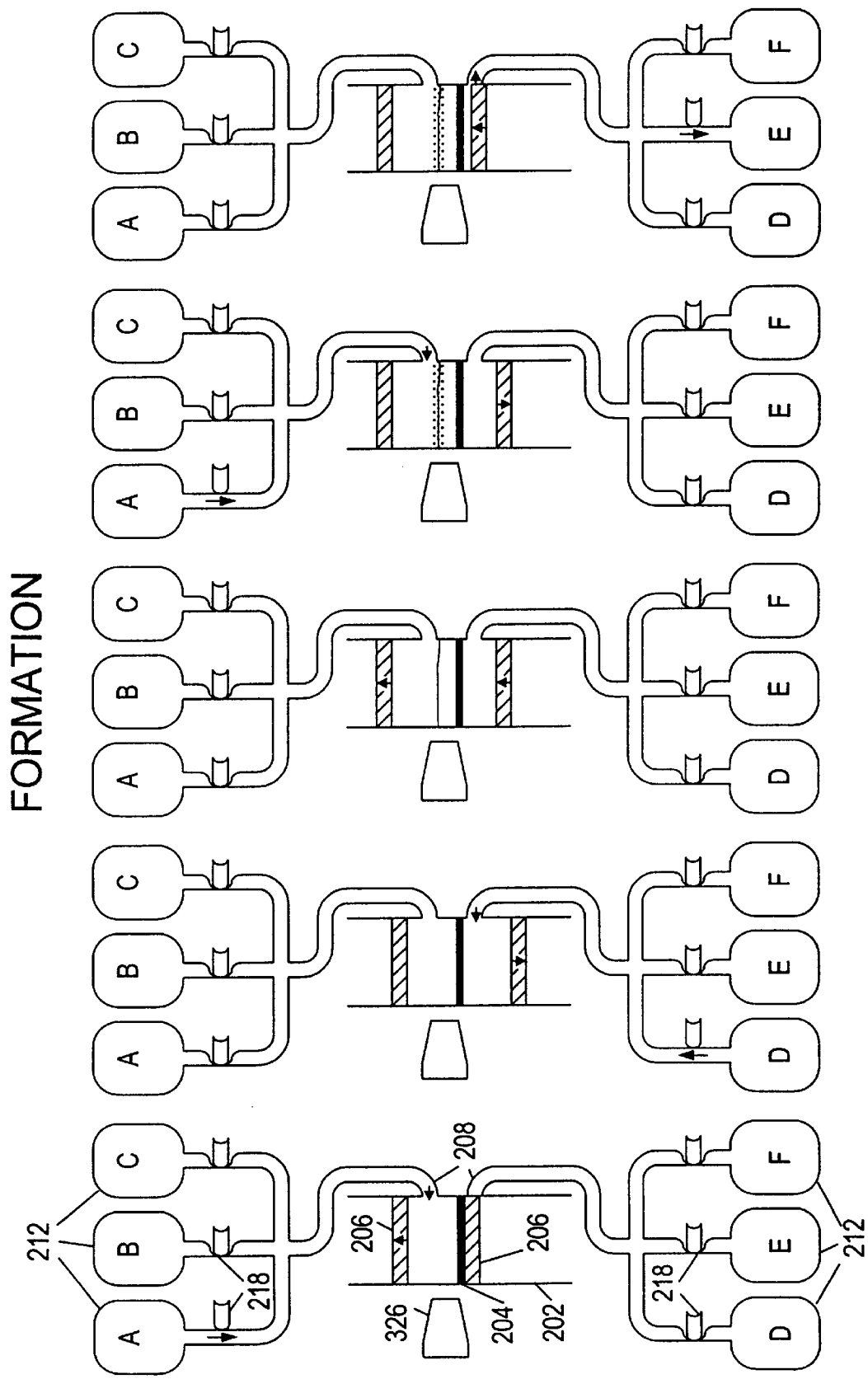

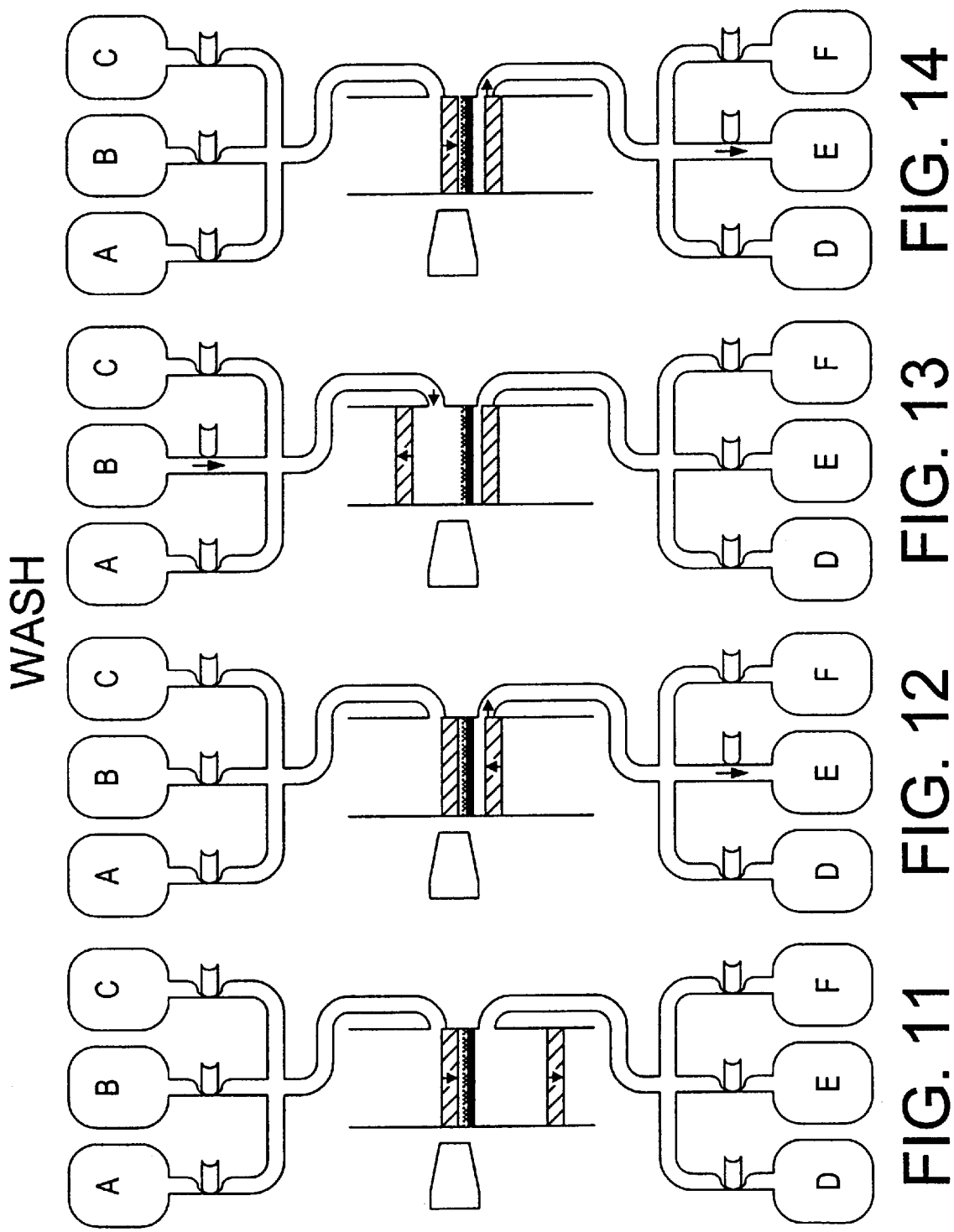

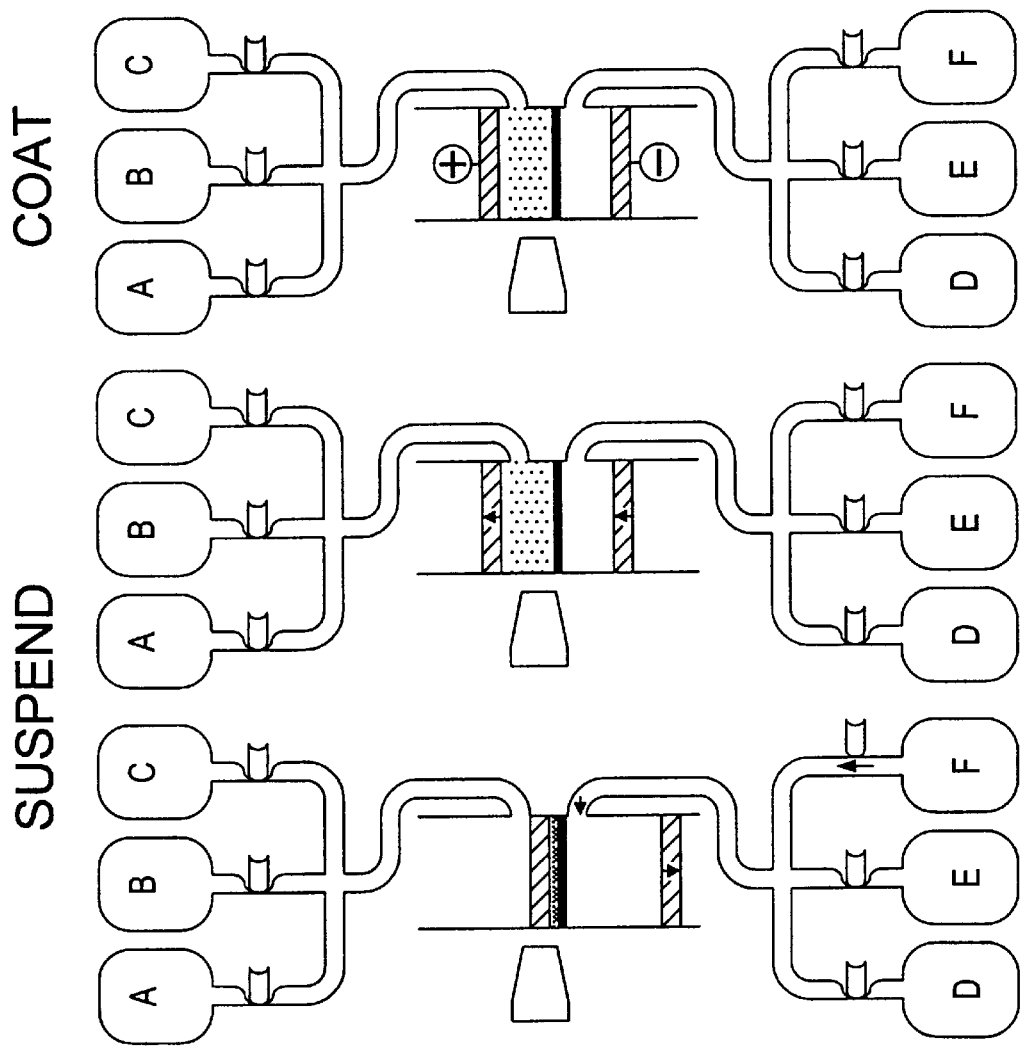

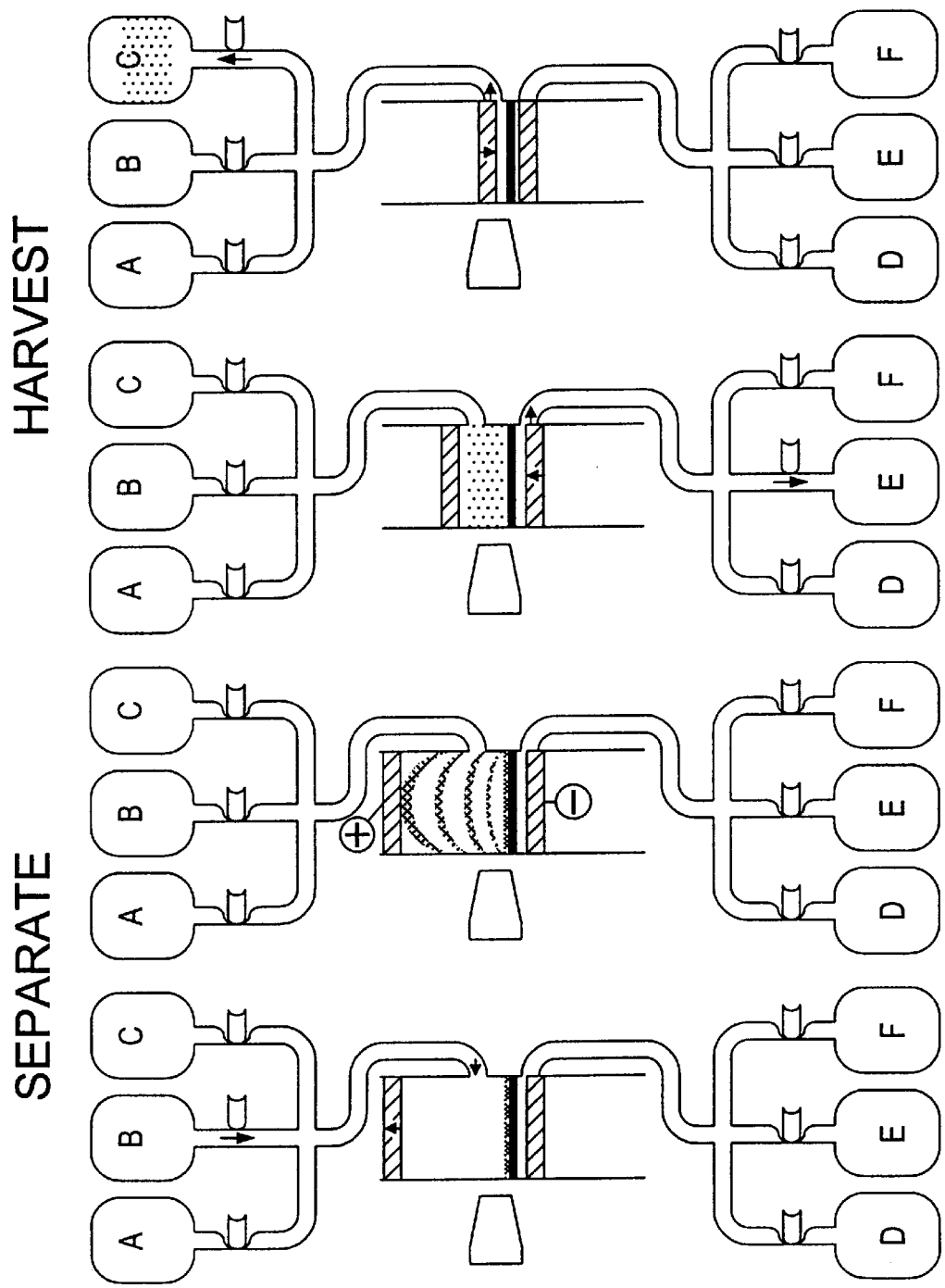

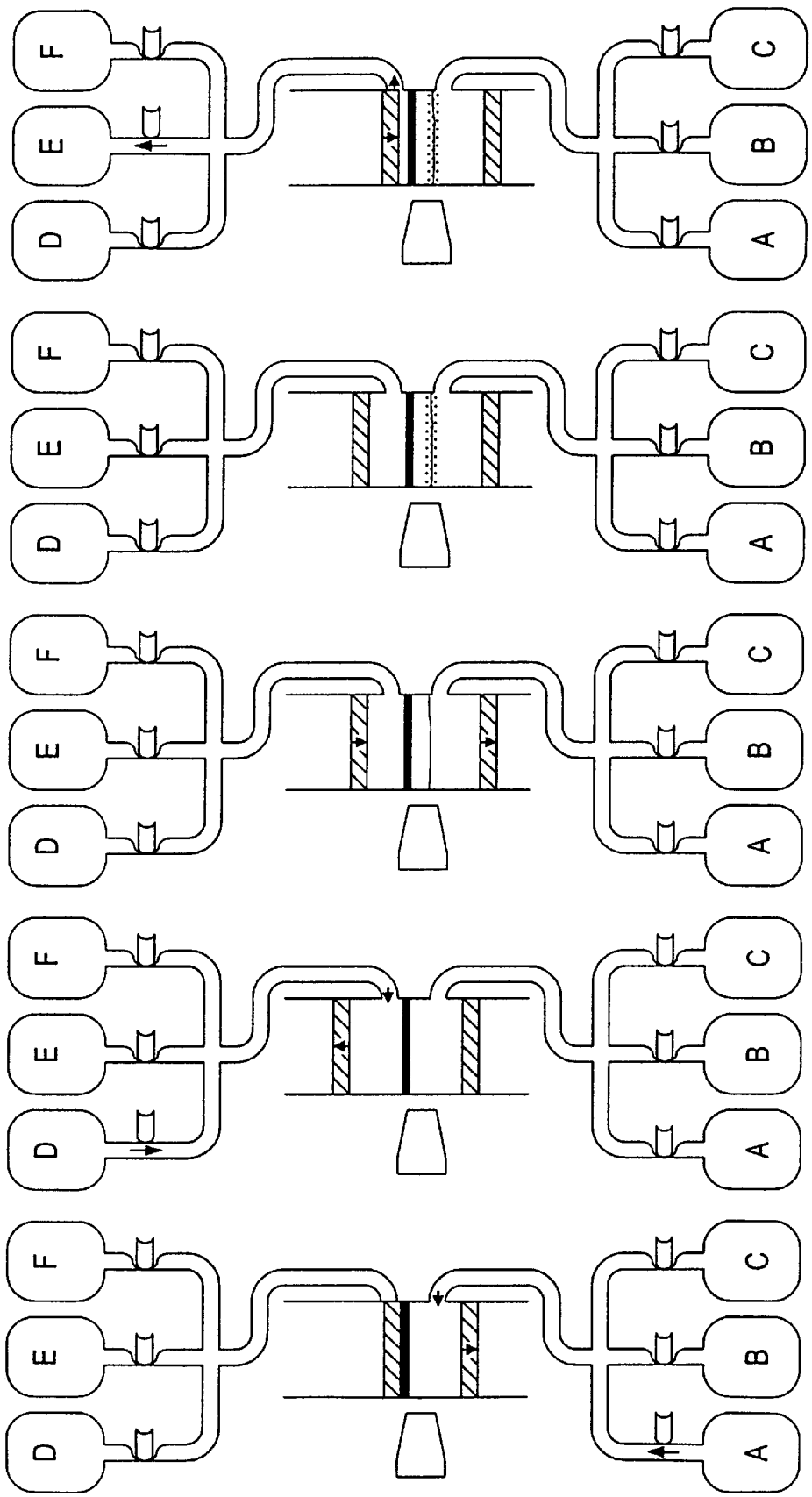

MICROENCAPSULATION AND ELECTROSTATIC PROCESSING DEVICE

CROSS-REFERENCE TO RELATED APPLICATIONS

This application is a continuation-in-part of U.S. patent application Ser. No. 08/349,169 filed Dec. 2, 1994 (now U.S. Pat. No. 5,827,531), which is hereby incorporated by reference as though completely set forth herein. This application is further related to the following U.S. Patent Applications which are filed contemporaneously herewith:

(1) Application Ser. No. 09/079,741 filed May 15, 1998, entitled "In Situ Activation of Microcapsules" invented by Dennis R. Morrison and Benjamin Mosier, NASA Case No. MSC22866-1;

(2) Application Ser. No. 09/079,758 filed May 15, 1998, entitled "Externally Triggered Microcapsules" invented by Dennis R. Morrison and Benjamin Mosier, NASA Case No. MSC22939-1-SB;

(3) Application Ser. No. 09/079,770 filed May 15, 1998, entitled "Low Shear Microencapsulation and Electrostatic Coating Process" invented by Dennis R. Morrison and Benjamin Mosier, NASA Case No. MSC-22938-1;

(4) Application Ser. No. 09/079,766 filed May 15, 1998, entitled "Microencapsulated Bioactive Agents and Method of Making" invented by Dennis R. Morrison and Benjamin Mosier, NASA Case No. MSC-22936-1-SB.

These applications are also hereby incorporated by reference as though completely set forth herein.

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

A. Field of the Invention

The invention relates to an apparatus for making microcapsules, encapsulating pharmaceutical compounds in microcapsules, microcapsules, microcapsule encapsulated pharmaceutical compositions and products, and methods of using the same.

B. Description of the Related Art

Many drugs and enzymes (e.g. cytotoxins or bioactive compounds) cannot be injected intravenously. Others can be injected, but rapidly degrade before reaching the target tissue. Some drugs and enzymes are cleared from the blood by the liver or kidneys so quickly that their biological half-life is too short to be of therapeutic value. Still other drugs are insoluble in aqueous solutions. Since intravenous injection in hydrocarbon solvents is not well tolerated by patients, such drugs are difficult to administer.

These limitations can be overcome by encapsulating the drugs inside small spheres or capsules which can be transported in the blood to the target and which can then release the drug directly to the target by diffusion. Properly designed microcapsules can provide unique methods of direct delivery by injection, nasal inhalation and dermal administration for sustained release of important bioactive drugs.

Solid matrix microspheres may also be used for transporting adsorbed drugs within the matrix. For instance, U.S. Pat. No. 4,492,720 to Mosier disclosed methods for making microspheres to deliver chemotherapeutic drugs (including Cis-Platinum) to vascularized tumors. This method of preparing microspheres is accomplished by liquid encapsulation and solid-phase entrapment wherein the water-soluble drug is dispersed in a solid matrix material. The method involves dissolving the aqueous drug and the matrix material in an organic solvent, in which they are mutually soluble, then dispersing this mixture in a second organic solvent to form an emulsion that is stable enough for intravascular injection.

Other solid-matrix approaches have utilized copolymers such as polyvinyl chloride/acrylonitrile dissolved initially in organic solvents to form microparticles containing aqueous enzyme solutions. U.S. Pat. No. 3,639,306 to Sternberg et al. discloses a method of making anisotropic polymer particles having a sponge-like inner support structure comprising large and small void spaces and an outer, microporous polymer film barrier. A multiple-step batch process is used which entails removal of the organic solvents used to dissolve the polymers prior to addition of aqueous components.

Solid-matrix microspheres, however, are often not perfect spheres thereby limiting the packing density. Additionally, many drugs cannot be trapped or adsorbed in these systems at effective concentrations and drug-release rates are typically cyclic due to higher diffusion rates from the surface than from the matrix core.

Microcapsules may provide encapsulation of higher concentrations and improved drug-release rates. "Microcapsule", as used herein, is a general term which can include any spherical liquid-filled microscopic vesicle surrounded by a semipermeable outer membrane, including, micelles, inverted micelles, bilayer vesicles, and multilamellar (multilayered) microcapsules which comprise at least two layers, one of which is innermost and is substantially completely enclosed within the other.

The size and shape of the microcapsules is critical. Microcapsule distribution and drug delivery behavior in the tissues is very sensitive to these parameters. Typically, microcapsules of roughly 1–20 micron diameter are optimum for intravenous administration, whereas, 30–300 micron diameter microcapsules are used for intraarterial delivery and 300 micron or greater for intraperitoneal administration.

Certain current methods of forming microcapsules (such as liposomes) are based on chemical characteristics of certain phospholipids that self-assemble into bilayers when dispersed in an excess of water. Most liposomes carry pharmaceuticals dissolved in the entrapped water. Drugs that are insoluble or that have only limited solubility in aqueous solvents pose problems for incorporation into liposomes. Such organic-soluble drugs are usually limited in liposomal formulations to those that bind inside the hydrophobic region of the liposome bilayer. Some drugs are so insoluble that they do not associate with the bilayer and, therefore, have very low encapsulation efficiencies. Certain liposomal drug formulations, including anti-tumor liposomes containing dexorubicin [Gabizion et al. 1992] or muramyltripeptide have been studied extensively in clinical trials. Many conventional therapeutic liposome microcapsules have natural phospholipid outer skins (usually in combination with cholesterol and fatty amine) and therefore are subject to elimination by immune cells. Other conventional methods use sialic acid and other coatings on the lipid bilayer to mask the liposomes from detection by the scavenging immune cells in the reticuloendothelial system (RES).

Conventional methods of forming microcapsules are based on liquid—liquid dispersions of aqueous drugs and organic solvents. The dispersion methods often require emulsification of the aqueous phase into organic carrier solutions by shear, bubbling or sonication. These methods typically produce water-in-oil (W/O) type liposomes, for which a second requisite step is the removal of the organic solvent (typically by evaporation) to form reverse-phase evaporation vesicles or stable plurilamellar vesicles. The size distribution for these vesicles is quite heterogeneous.

These methods are limited because the density-driven phase separation results in the need to use multi-step, batch processing including mechanical mixing and solvent evaporation phases. Each batch step suffers losses which reduce overall efficiencies. Typically, in order to generate multilamellar vesicles, film casting with organic solvents, hydration and sizing using filtration through inert membrane filters is required [Talsma and Crommelin 1992]. Sophisticated, multi-step emulsion technology is required and yields of uniform type and size are often very low.

For instance, U.S. Pat. No. 4,855,090 to Wallach, discloses a method of making a multilamellar lipid vesicle by blending an aqueous phase and a nonaqueous lipophilic phase using a high shear producing apparatus. The lipophilic phase is maintained at a high temperature (above the melting point of the lipid components) and is combined with an excess of the aqueous phase, which is also maintained at a high temperature. U.S. Pat. No. 5,032,457 to Wallach discloses a paucilamellar lipid vesicle and method of making paucilamellar lipid vesicles (PLV). The method comprises combining a nonaqueous lipophilic phase with an aqueous phase at high temperatures and high shear mixing conditions, wherein the PLVs are rapidly formed in a single step process. U.S. Pat. No. 4,501,728 to Geho et al. discloses the encapsulation of one or more drugs or other substances within a liposome covered with a sialic acid residue for masking the surface of the membrane from scavenging cells of the body utilizing techniques known for the production of liposomes. In one embodiment, additional tissue specific constituents are added to the surface of the liposome which cause the liposome thusly treated to be attracted to specific tissues. Similarly, U.S. Pat. No. 5,013,556 to Woodle et al. provided methods for making liposomes with enhanced circulation times. Liposomes created by this method contain 1–20 mole % of an amphipathic lipid derivatized with a polyalkylether (such as phosphatidyl ethanolamine derivatized with polyethyleneglycol). U.S. Pat. No. 5,225,212 to Martin et al. discloses a liposome composition for extended release of a therapeutic compound into the bloodstream, the liposomes being composed of vesicle-forming lipids derivatized with a hydrophilic polymer, wherein the liposome composition is used for extending the period of release of a therapeutic compound such as a polypeptide, injected within the body. Formulations of "stealth" liposomes have been made with lipids that are less detectable by immune cells in an attempt to avoid phagocytosis [Allen et al. 1992]. Still other modifications of lipids (i.e., neutral glycolipids) may be affected in order to produce anti-viral formulations (U.S. Pat. No. 5,192,551 to Willoughby et al. 1993). However, new types of microcapsules are needed to exploit the various unique applications of this type of drug delivery.

Processes and devices are needed for forming spherical multilamellar microcapsules having alternating hydrophilic and hydrophobic liquid layers, surrounded by flexible, semi-permeable hydrophobic or hydrophilic outer membranes which can be tailored specifically to control the diffusion rate. In particular, devices for making such microcapsules are needed which do not rely on batch processes involving mechanical mixing and solvent evaporation phases. Moreover, there is clearly a need for methods, devices, and compositions which allow for larger and somewhat uniformly sized microcapsules which have the ability to carry larger amounts of drug and/or more than one drug within a semi-permeable outer membrane, possibly dissolved in different solvent phases within the outer membrane. Such improved microcapsules would be particularly useful in the delivery of pharmaceutical compositions.

REFERENCES CITED

The following references to the extent that they provide procedural details supplementary to those set forth herein, are specifically incorporated herein by reference.

Allen, T. M., Mehra, T., Hansen, C. and Chin, Y. C., Stealth Liposomes: An Improved Sustained Release System for 1-b-D-Arabinofuranosylcytosine, Cancer Res. 52:2431–39, 1992.

Gabizon, A., et al., Liposome-Associated Doxorubicin: Preclinical Pharmacology and Exploratory Clinical Phase, in G. Lopez-Berestein and I. J. Fidler (Eds.) *Therapy of Infectious Diseases and Cancer*, Alan R. Liss, Inc., New York, pp. 189–203, 1992.

Talsma, H. and Crommelin, D. J. A., Liposomes as Drug Delivery Systems, Part 1: Preparation. Pharmaceutical Technology, pp. 96–106, October 1992.

SUMMARY OF THE INVENTION

Accordingly, there is provided herein a microencapsulation and electrostatic processing device for forming microcapsules. In one embodiment, the device comprises a chamber having a planar, porous membrane (e.g. a filter) which separates a first region in the chamber from a second region in the chamber. An aqueous solution is introduced into the first region through an inlet port, and a hydrocarbon solution is introduced into the second region through another inlet port. The filter acts to stabilize the interface and suppress mixing between the two immiscible solutions as they are being introduced into their respective regions. After the solutions have been introduced and have become quiescent, the interface is gently separated from the filter. At this point, spontaneous formation of microcapsules at the interface may begin to occur, or some fluid motion may be provided to induce microcapsule formation. In any case, the fluid shear force at the interface is limited to less than about 100 dynes/cm$^2$. This low-shear approach to microcapsule formation yields microcapsules with good sphericity and desirable size distribution. The microencapsulation and electrostatic processing device may also be capable of downstream processing of microcapsules, including rinsing, re-suspension in tertiary fluids, electrostatic deposition of ancillary coatings, and free-fluid electrophoretic separation of charged microcapsules.

In one embodiment, the microencapsulation device relies on liquid—liquid interactions for microcapsule formation. Although the exact mechanisms are not fully understood, the inventors believe that the maintenance of certain surface properties, such as the surface tension, Helmholtz charge distribution (electrical double layer), and partitioning of surfactant molecules between two immiscible fluids must remain substantially intact so that lateral phase separation can occur in a manner which allows simultaneous formation of multiple liquid interfaces (oil/water or water/oil) and which results in microcapsules having alternating spherical shells of hydrophilic and hydrophobic liquid layers.

Although this can best be demonstrated under microgravity conditions, wherein buoyant convection is absent and diffusion-driven convection predominates, the inventors have found that using the methods and devices described herein that microcapsule formation can also be accomplished in unit gravity conditions by balancing the density differences between the two fluids or by mechanical means which prevents excess fluid shear from significantly altering the normal adsorptive surface properties which are determined by the chemical composition of the fluids and the interfacial phenomena among their solvents, polymers and surfactants. In one implementation, the two fluids are allowed to interact at their interface without agitation, stirring, shearing or like force, and even quiescent forces such as gravity-controlled sedimenting, shifting, and drift are limited. Thus, in this implementation only chiefly diffusion-driven convection and surface tension is used to spontaneously form microcapsules, as the chemical formulations of the different fluids assist in lowering the surface free energy across the interface. As the microcapsules form, a polymeric outer coating is created by interfacial coacervation.

Before operation of the microencapsulation device, two fluids are first formulated. The fluids are substantially immiscible, i.e. the fluids have sufficiently different densities, viscosities, and/or surface tensions which permit the formation of an interface, and at least one component of a particular fluid is not soluble more than 10 g/100 ml in the other fluid. Formulation of the first fluid comprises combining a first solvent, a first polymer soluble in the first solvent, a co-solvent, an oil, and water. The first solvent will typically form about 75–90% by volume of the first fluid, the first polymer about 1–5%, the oil about 1–10%, and the water about 1–5%. A small amount of a co-solvent is also included in the first fluid, and may function as a co-surfactant. Oil comprising about 1–10% by volume is also added to the formulation. The first fluid can also contain about 1–5% water by volume.

Formulation of the second fluid comprises combining a second solvent, a second polymer soluble in the second solvent, a surface active agent, and a salt. The relative, approximate volume percentages of these constituents is about 70–98% second solvent, 1–10% second polymer, 1–4% surface active agent, and 0–3% salt. In order to ensure that the liquid—liquid interactions necessary to form the microcapsule will occur, certain of the constituents of each fluid are selected relative to one another. Thus, the surface active agent in the second fluid is selected such that it will have a hydrophilic/lipophilic balance value greater than that of the first polymer constituent of the first fluid. Generally, the most useful surface active agents have been found to be those which are nonionic and which have a hydrophilic/lipophilic balance value of 10.0 or greater. Next, the second polymer constituent of the second fluid is selected to have a hydrophilic/lipophilic balance value lower than that of the surface active agent constituent of the same fluid, but greater than the hydrophilic/lipophilic balance value of the first polymer. While not an exhaustive list, certain hydrophilic/lipophilic balance values of materials which may be used in the formulations of the invention are provided in the parent application.

The microcapsules which result from these formulations are unilamellar (single layer) microcapsules or multilamellar (multi-layer) microcapsules having alternating hydrophilic and hydrophobic liquid layers and surrounded by flexible, semi-permeable, hydrophobic, outer membranes. These outer membranes can be advantageously tailored specifically to control the diffusion rate of pharmaceuticals released from within. Encapsulation of cytotoxic or labile drugs in such microcapsules enables targeted delivery and sustained release kinetics that are not currently available with intravenous injection. Radiocontrast media may also be advantageously enclosed within the microcapsules to provide for tracking and improved dosage determinations.

BRIEF DESCRIPTION OF THE DRAWINGS

FIG. 1a is a table summarizing fluid formulations for use in the microencapsulation and electrostatic processing device.

FIG. 1b is a table summarizing one formulation strategy for the formation fluids to be used in the microencapsulation and electrostatic processing device.

FIG. 1c is a table summarizing a second formulation strategy for the formation fluids.

FIG. 1d is a table summarizing other fluid formulation ingredients for use in the microencapsulation and electrostatic processing device.

FIGS. 6–26 are schematic illustrations of steps in the microcapsule formation process.

DETAILED DESCRIPTION OF THE INVENTION

A. Formulation of the Fluids

Figure 2:
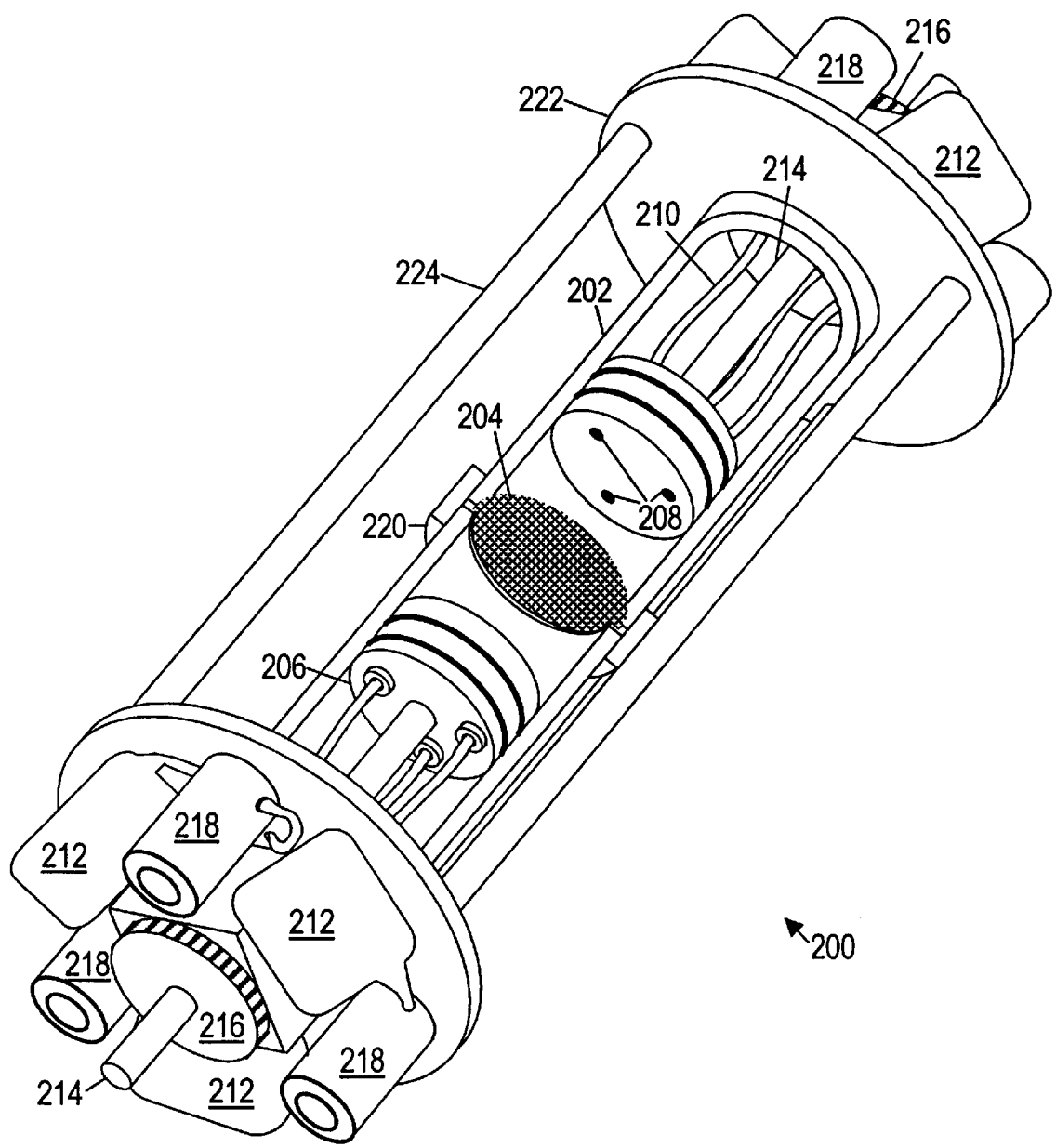
FIG. 2 illustrates one embodiment of a microencapsulation and electrostatic processing device.

The microencapsulation procedure begins with the formulation of two liquid solutions which are immiscible with each other. Formulation of the first fluid comprises combining a first solvent, a first polymer soluble in the first solvent, a co-solvent, an oil, and water. The first solvent will typically form about 75–90% by volume of the first fluid, the first polymer about 1–5%, the oil about 1–10%, and the water about 1–5%. A small amount of a co-solvent can also be included in the first fluid, and may function as a co-surfactant Formulation of the second fluid comprises combining a second solvent, a second polymer soluble in the second solvent, a surface active agent, and a salt. The relative, approximate volume percentages of these constituents is about 70–98% second solvent, 1–10% second polymer, 1–4% surface active agent, and 0–3% salt. In order to ensure that the liquid—liquid interactions necessary to form the microcapsule will occur, certain of the constituents of each fluid are selected relative to one another. Thus, the surface active agent in the second fluid is selected such that it will have a hydrophilic/lipophilic balance value greater than that of the first polymer constituent of the first fluid. Generally, the most useful surface active agents have been found to be those which are nonionic and which have a hydrophilic/lipophilic balance value of 10.0 or greater. Next, the second polymer constituent of the second fluid is selected to have a hydrophilic/lipophilic balance value lower than that of the surface active agent constituent of the same fluid, but greater than that of the first polymer constituent of the first fluid. While not an exhaustive list, certain hydrophilic/lipophilic balance values of materials which may be used in the formulations of the invention are provided in the parent application.

The formulation procedure differs slightly depending upon whether the first solvent is selected to be organic or aqueous. Where an organic solvent is used to formulate the first liquid solution, that organic solvent may be selected from the group of organic solvents consisting of ethyl alcohol, methyl alcohol and isopropyl alcohol. The first polymer is then selected to be one soluble in the selected organic solvent. Such a first polymer may be selected from the group of polymers consisting of glycerol monostearate, glycerol monooleate, glycerol monolaurate, glycerol dioleate, glycerol distearate, cholesterol, stigmasterol, phytosterol, campesterol, and lecithins such as phosphatidyl cholines (e.g., Centrolex-F™).

Where the first solvent is aqueous, the first polymer is again requisitely soluble in the selected aqueous solvent, and may be selected from the group of polymers consisting of polyvinyl pyrrolidone, polyvinyl alcohols, gelatin, gum tragacanth, carrageenan, Karaya gum, Guar gum, gum arabic alginates, carboxymethyl cellulose, hydroxypropyl cellulose, carboxypropyl cellulose, and lecithins.

Regardless of the formulation with an aqueous or organic first solvent and polymer, the co-solvent may be selected from the group of co-solvents consisting of $C_3$–$C_8$ alcohols, tetrahydrofuran, dioxane, acetonitrile, dimethylformamide, dimethylacetamide, and dimethyl sulfoxide. Similarly regardless of the organic/aqueous nature of the first solvent, the oil may be selected from the group of oils consisting of unsaturated oils such as poppy seed oil, olive oil, peanut oil, sesame oil, cotton seed oil, soybean oil, safflower oil, corn oil, sunflower seed oil and canola oil or saturated oils such as mineral oil, long chain paraffinic oil, and liquid petrolatum. In one embodiment, poppy seed oil is selected and iodinated to form iodinated poppy seed oil (IPO), which is then incorporated into microcapsules and serves as a marker or tracer for tracking via radiocontrast detection methods known well to those of skill in the art of radiography.

The formulation of the second fluid uses a second solvent immiscible in the first solvent. Whether an organic or an aqueous solvent is chosen, the second polymer, the surface active agent and the salt may each be selected from a particular group of such compounds. The second polymer may be selected from the group of polymers consisting of polyethyleneglycol 400–20000 daltons, dextran 1000–100,000 daltons, polyvinylpyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, cyclodextrins, and lecithins. It is noted that the second polymer is selected to have a hydrophilic/lipophilic value greater than that of the polymer in the first fluid. The surface active agent is selected from the group of surface active agents consisting of sorbitan monooleate treated with ethylene oxide, dextran, polyethylene glycol, $C_{12}$–$C_{20}$ fatty acids, 2-amino-2-methyl-1-propyl aminomethyl propanol amphoteric salts and quaternary ammonium salts. It is noted that the surface active agent is selected to have a hydrophilic/lipophilic balance value greater than that of the second polymer. The salt is selected from the group of salts consisting of NaCl, KCl, $CaCl_2$, $MgCl_2$, quaternary ammonium salts (such as acetyl trimethylammonium bromide), 2-amino-2-methyl-1-propyl aminomethyl propanol and 4-methoxy-4(3-phosphatidyl choline)spiro(1,2-dioxetane-3-g,1-adamantane) disodium salt. Use of neutral salt solutions enhances micelle formation and lateral phase separation, and increases the dispersion of microcapsules and their stability as they are formed.

Injectable polysaccharides similar to those found in Ringer's solutions may be included in the fluid formulations. The polysaccharides contribute to the driving forces that control phase separation and phase partitioning of the entrapped drugs. The polysaccharides also provide increased shelf-life and stability of the parenteral suspensions.

The pharmaceutical composition to be encapsulated in the microcapsule may be one soluble in aqueous solutions or may be one soluble in organic solutions. This, of course, governs the selection of the fluid in which the pharmaceutical composition is formulated. The ability to encapsulate organic-soluble pharmaceuticals is particularly advantageous as these types of drugs are otherwise very difficult to administer. The pharmaceuticals may be those selected from the group of such widely diversified pharmaceutical compositions as that consisting of cytotoxins, proteases, cytokines, anti-nauseants, steroids, anti-fungal agents, fibrinolytic enzymes, antibiotics, and photoactivated drugs. The inventors have successfully encapsulated representatives of these classes of pharmaceuticals using the methods of the invention.

It is also possible to incorporate a pharmaceutical composition which is not initially dissolved in one or another of the fluids or layers, but rather which drug is in suspension. As noted above, depending upon its solubility and upon where the pharmaceutical chemist wishes to locate the drug, it is possible to formulate a drug in either of the liquids, by dissolving or suspending the drug as needed.

Microcapsules, once formed, may undergo additional steps. These steps may include washing, coating, electrophoretic separation, suspension in a storage solution, and activation immediately prior to injection. Additional fluids may be provided for these steps. These additional steps may be used to advantageously provide the microcapsule with specific characteristics. For example, a washing step with a wash fluid may be used to "cure" the outer membrane of the microcapsule or otherwise enhance the ruggedness of the microcapsule. Or, a coating step may be used to add a pharmaceutical composition to the formed surface of the microcapsule. Instances of this include an adjuvant which comprises an immunoglobulin, another protein, a hydrocolloid or a polysaccharide. These coatings may be particularly useful for producing microcapsules with unique immunologic, proteinaceous, surface charge, or other surface characteristics which makes them selectively adhere to certain target tissues (cells), or renders the microcapsules less or more attractive to certain phagocytic immune cells (e.g. when these cells are the actual target for the therapeutic drug). Where the adjuvant is a hydrocolloid, it may be selected from the group of such hydrocolloids consisting of collagen, isoelectric gelatin, agar, gum arabic, gum tragacanth, alginates, cellulose derivatives and carrageenans.

The coating fluid may be identical to the wash fluid mentioned earlier. The coating fluid includes coating compounds which may or may not be present in the wash fluid. Fluids for coating microcapsules may include anionic, cationic or amphoteric compounds which may be actively (e.g. with the aid of an electric field) or passively deposited on the surface of the microcapsules to alter the surface charge or zeta potential of the microcapsules. Instances of such coating materials include PEG and PVP. In some other instances the coating fluid may comprise uncharged substances such as an oil or $C_{14}$–$C_{60}$ paraffin for coating the formed microcapsules.

Coating fluids may also contain a chemical activator which acts upon the inactive form of the pharmaceutical agent (drug) as is diffuses out of the inner layers of the microcapsule. The function of the activator would be to chemically convert the inactive drug to its active form just before it is released from the microcapsule. This is illustrated when the pharmaceutical is a pro-enzyme and where the activator is another proteolytic enzyme which cleaves the pro-enzyme at active site to render the molecule biologically active. This embodiment can be used to deliver very labile drugs which have very limited shelf-lives or short biological half-lives and can maximize the therapeutic effectiveness of the short-lived drug at the target site of action.

Fluids for electrophoretic separations are primarily low conductivity solutions such as water, or aqueous solutions with very low salt or ion content (typically less than 0.01 molar when using field strengths of 10 V/cm or greater, and preferably conductivities of $1.5 \times 10^{-3}$ to $1 \times 10^{-5}$ mho/cm or less). Other substances may be added to the low conductivity solutions as necessary to provide an osmotic balance and/or a salt balance across the microcapsule membrane. These solutions may also serve as storage solutions.

FIG. 1a provides a high-level summary of fluids which were discussed above. FIG. 1b provides a more detailed example of one formulation strategy for the microcapsule formation fluids, and FIG. 1c provides a second example of a formulation strategy for the microcapsule formation fluids. FIG. 1d provides examples of ingredients for additional fluids which may be used for coating, separating, and storing formed microcapsules.

B. Microencapsulation Devices

Turning now to FIG. 2, a first embodiment 200 of a microencapsulation device is shown. Device 200 comprises chamber 202, filter 204, plungers 206, inlet/outlet ports 208, tubes 210, reservoirs 212, shafts 214, motors 216, valves 218, central support member 220, and support frame components 222 and 224. Device 200 is configured to create a quiescent, planar interface between two immiscible fluids whereby microcapsule formation occurs in a largely spontaneous manner due to interfacial coacervation or under controlled fluid shear along the immiscible fluid interface. Device 200 is consequently configured to maintain precise control over fluid flows and fluid shear along the interface. Device 200 may be further configured to concentrate, rinse, coat, flush, and harvest microcapsules after they have formed, all without removing the microcapsules from the original process chamber. The method of operation is discussed further below.

Chamber 202 comprises an inert, preferably transparent, material such as polycarbonate plastic, glass or Pyrex®. A cylindrical shape is preferred but not strictly necessary. A filter 204 is positioned transversely within the chamber 202 to separate the chamber into two regions. Filter 204 is a porous membrane which is initially used to stabilize the interface between the two fluids, but which may later be used for harvesting microcapsules. For this later use, the filter 204 is provided with a characteristic pore size which will screen larger particles from a fluid flow and allow smaller particles to pass through. Depending on the formulation, the characteristic pore size may range from 1 to 300 microns, and may preferably have a pore size up to 100 microns and most preferably have a pore size up to 25 microns. Filter 204 preferably comprises inert materials which are non-wetting to the microcapsule's outer coating (i.e. contact angle is less than 90°). Nylon and polypropylene are examples of such materials.

It is noted that in one embodiment, device 200 rests in a gimbaled assembly (not shown) which allows 180 degree inversion and at least some horizontal tilt in either direction along a perpendicular axis to facilitate fluid loading and unloading and to assist in removal of air bubbles from chamber 202. In a preferred embodiment, the device is operated in a vertical orientation when in a gravitational field so that the filter 204 is horizontally disposed within chamber 202. Hereafter, references to the "upper plunger" or the "upper region of chamber 202" refer to the plunger and region which would be above filter 204 during processing in a gravitational field. Similarly, references to the "lower plunger" or the "lower region of chamber 202" refer to the plunger and region which would be below filter 204 during processing in a gravitational field.

Chamber 202 is sealed on two ends by plungers 206. The plungers 206 may be comprised of aluminum, stainless steel, Ultem™ (a rigid polymer), or similar materials which are inert but easily machined. For device 200, inlet/outlet ports 208 are provided in the plunger faces, but they may alternatively be positioned on the side walls of chamber 202. The inlet/outlet ports 208 are coupled to fluid reservoirs 212 via flexible tubes 210. The reservoirs 212 may take the form of collapsible pouches, as shown, or they may be provided in the form of syringes, ventilated containers, pressurized cannisters, etc. The number of reservoirs 212 in device 200 may be variable, ranging from at least two to as many as desired. In device 200, the inflow or outflow of fluids will be driven by pressure differentials created by piston-like motion of plungers 206. As is discussed further below, the plungers 206 may additionally be provided with electrodes, pressure transducers, and/or temperature sensors on the plunger faces. The electrodes may be used for electrostatic processing of microcapsules, and the pressure and temperature sensors may be used for monitoring and feedback control of the microcapsule formulation process. The electrodes, pressure transducers, and/or temperature sensors may also alternatively be located elsewhere on the chamber walls or filter surfaces.

The plungers 206 are driven axially in chamber 202 by motors 216 via threaded rods 214. Motors 216 are preferably stepper motors which provide high torque at extremely slow speeds. Shafts 214 are preferably electrically non-conductive. As the motor actuators pivot, they cause shafts 214 to move in or out, which causes the plungers 206 to move correspondingly, thereby displacing fluid into or out of chamber 202. This embodiment allows the upper plunger and lower plunger to be moved independently of each other while the processing chamber 202 and intermediary membrane 204 remain fixed. The upper and lower regions of the chamber together form a closed system, wherein movements of either plunger provide positive or negative pressure on the fluids, so that when one of the valves 218 is open, fluids are slowly moved into or out of the chamber 202. The simultaneous, unidirectional movement of the plungers 206, when all valves 218 are closed, serves to move the immiscible fluid interface away from the filter 204.

The various reservoirs may be made accessible or inaccessible to chamber 202 by valves 218. Each reservoir 212 is provided with a valve 218. Valves 218 may be solenoid-driven pinch valves which close the reservoirs by pinching tubes 210. The valves 218 are usually closed, and consequently normally-closed valves may be preferred.

Support member 220 acts as a holder for filter 204 and a sealing gasket which separate the two regions of chamber 202, and may further serve as a coupler for two pieces used to form chamber 202. In this embodiment, filter 204 is a replaceable membrane filter.

Figure 3:
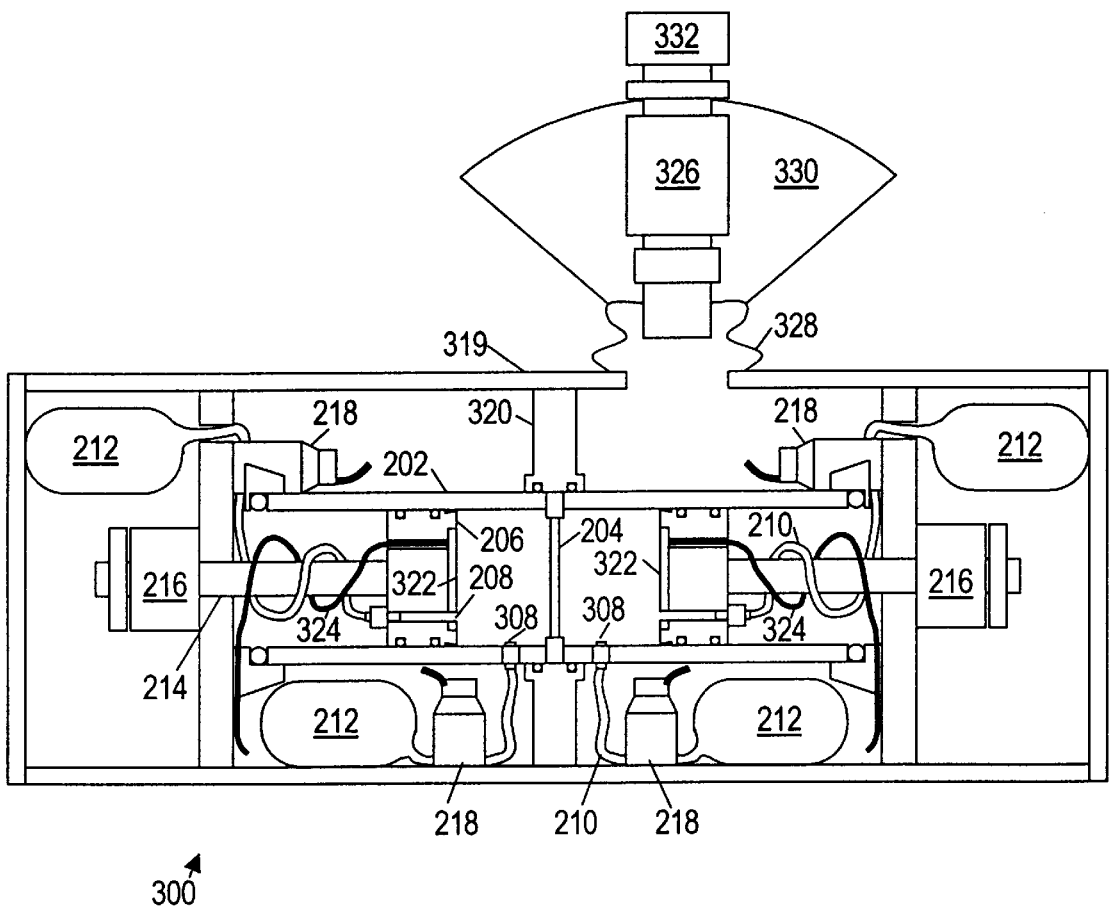
FIG. 3 illustrates another embodiment of a microencapsulation and electrostatic processing device.

FIG. 3 shows a cross-sectional view of another embodiment 300 of a microencapsulation device. In addition to chamber 202, filter 204, plungers 206, inlet/outlet ports 208, tubes 210, reservoirs 212, shafts 214, motors 216, and valves 218, device 300 comprises side inlet/outlet ports 308, casing 319, support member 320, electrodes 322, conductors 324, camera 326, boot 328, camera mount 330, and motor 332. Device 300 is configured to create a quiescent interface between two immiscible fluids to provide for microcapsule formation, and is further configured to electrostatically coat microcapsules after they have been formed. The method of operation is discussed further below.

Rather than an open-cage structure, device 300 (in FIG. 3) is provided with a closed-box structure. Although various elements such as inlet/outlet ports 308, reservoirs 212 and valves 218 are placed differently than in device 200, their functions are preserved. Support member 320 in this embodiment supports filter 204 and chamber 202. The plungers 206 are shown with electrodes 322 on their faces. In one embodiment, the electrodes are composed of or plated with palladium, which is an inert conductive metal. The electrodes 322 are coupled by conductors 324 to a high voltage power supply (not shown).

A camera 326 is coupled to the casing 319 of device 300 via a boot 328 and a camera mount 330. A positioning motor 332 is configured to position the camera at various angles on the camera mount 330. In one embodiment, the camera is a video microscope camera which can be focused on the region in chamber 202 near filter 204 to monitor the formation of microcapsules. An illumination source (not shown) may be provided with camera 326. If desired, a camera can also be used in the embodiment of FIG. 2.

Figure 4:
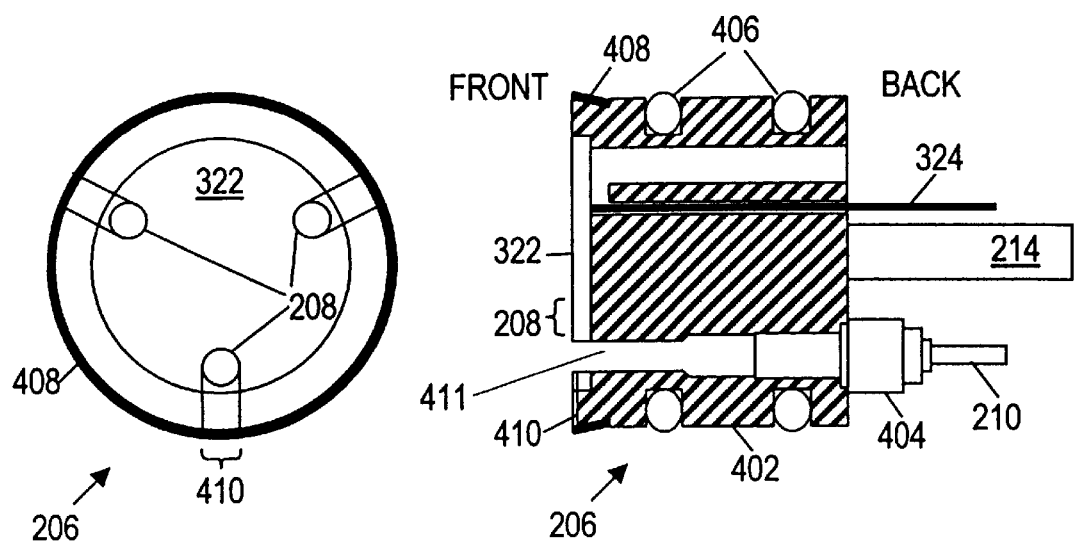
FIG. 4 illustrates an exemplary plunger for use in a microencapsulation device.

FIG. 4 shows two views of one embodiment of plunger 206. Plunger 206 comprises piston head 402 having inlet/outlet ports 208, electrode 322, bubble wiper 408, bubble-chasing grooves 410, and O-rings 406. Shaft 214, conductor 324 and connector 404 are also shown. Inlet/outlet ports 208 are formed in the face of piston head 402 and coupled by passages 411 to connectors 404 on the back of piston head 402. Connectors 404 serve to connect tubes 210 to the piston head 402. Electrode 322 is attached to the face of piston head 402 and connected to conductor 324 which passes through a passage to the back to piston head 402. In an alternate embodiment, the piston head itself serves as an electrode.

Bubble wiper 408 is a flexible gasket material which serves to seal the face of plunger 206 to the wall of chamber 202 to prevent bubbles from getting trapped between the piston head 402 and the chamber wall. In one implementation, fluorinated ethylene propylene (a Teflon-like material) may be used as the bubble wiper 408. "Bubble chasing" grooves 410 are also provided in the face of piston head 402, and they connect with inlet/outlet ports 208 to facilitate gas bubble removal from chamber 202. Slots are also provided in piston head 402 to hold O-rings 406 which provide a liquid pressure seal with the wall of chamber 202.

Figure 5:
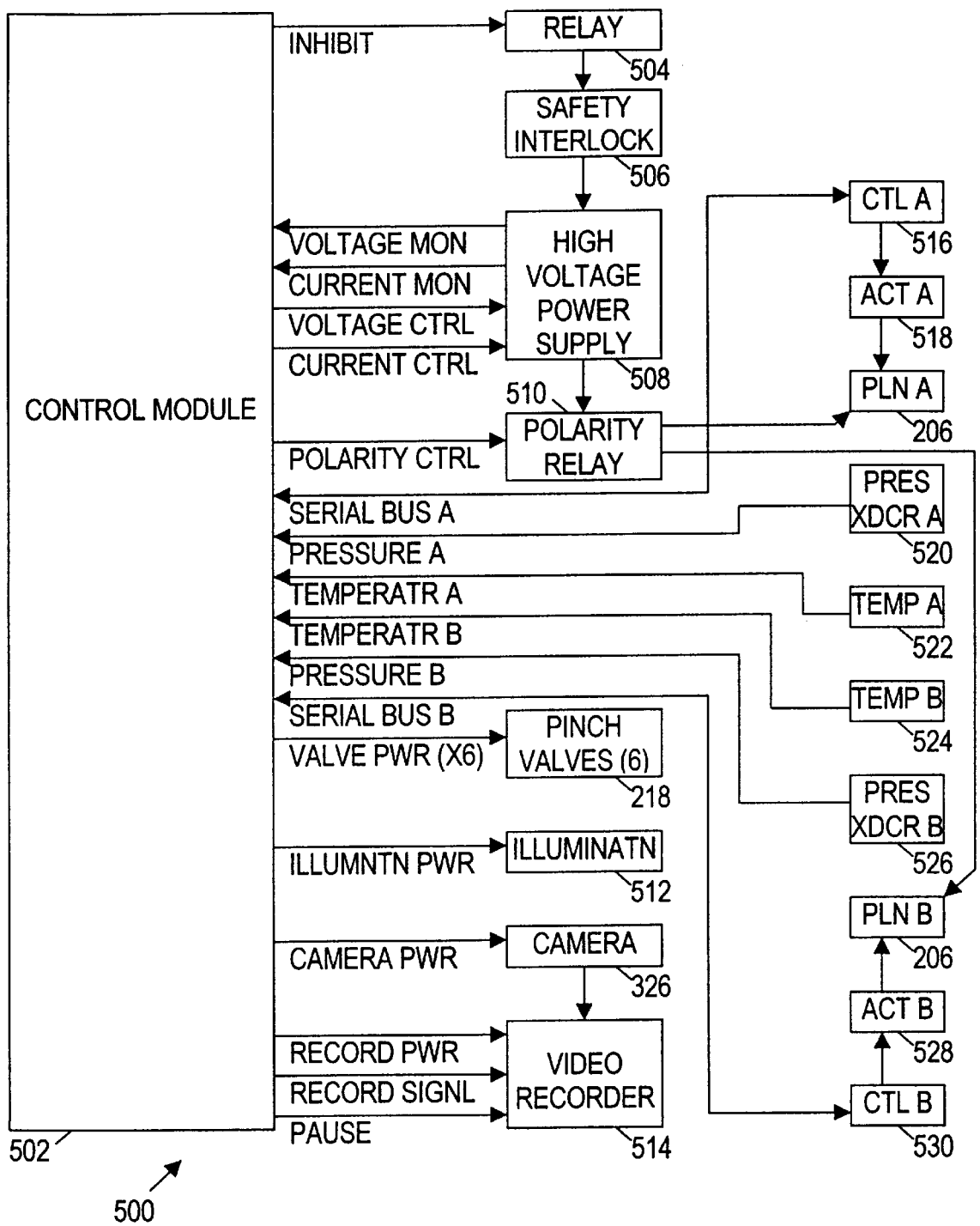
FIG. 5 is a block diagram of one embodiment of a microencapsulation and electrostatic processing device's electrical sub-system.

FIG. 5 shows an electrical signal flow diagram of an embodiment of a microencapsulation device control system 500. It comprises control module 502, relay 504, safety interlock 506, high voltage power supply 508, polarity relay 510, pinch valves 218, illumination source 512, camera 326, video recorder 514, controllers 516 and 530, actuators 518 and 528, plungers 206, pressure transducers 520 and 526, and temperature sensors 522 and 524. Control module 502 preferably operates the various components of control system 500 in a sequential manner to perform microcapsule formation and other pre- and post-formation processing steps. In one embodiment, control module 502 comprises a programmable computer which executes steps stored in a memory, and monitors and records useful observation parameters. In another embodiment, control module 502 includes a user interface module having switches and digital readouts which allow the user to trigger and operate the various components as desired to perform the necessary microcapsule formation steps.

Control module 502 is coupled to provide an INHIBIT signal to power relay 504, whereby high voltage power supply 508 may be turned on or off. A safety interlock 506 may also be provided to disable the high voltage power supply 508 when the casing is opened. Control module 502 is further coupled to provide VOLTAGE CONTROL and CURRENT CONTROL signals to high voltage power supply 508 to regulate the current and/or voltage generated. Feedback signals VOLTAGE MONITOR and CURRENT MONITOR from the high voltage power supply 508 may be supplied to control module 502 for improved voltage and current regulation and to provide useful observation parameters to the user. The output of high voltage power supply 508 is connected to plungers 206 via polarity relay 510 and conductor 324 (FIG. 3). Polarity relay 510 serves to reverse the polarity of the voltage applied between the plungers 206 as dictated by the POLARITY CONTROL signal provided from the control module 502. The high voltage power supply may be configured to supply as much as 500 V/cm between the plungers 206 if such is desired.

Control module 502 is also coupled to provide an ILLUMINATION POWER signal to illumination source 512 to turn the illumination source 512 on and off. Similarly, the control module 502 is coupled to provide a CAMERA POWER signal to camera 326 to turn the camera 326 on and off, and a RECORDER POWER signal to video recorder 514 to turn the video recorder 514 on and off. The control module 514 may further be coupled to provide PAUSE and RECORD signals to video recorder 514 to control its operation. In one embodiment, the camera 326 is a video microscope which may be used to monitor fluid flows and microcapsule formation within chamber 202.

Control module 502 is coupled to provide an individual VALVE POWER signal to each pinch valve 218 in device 502 to open and close each valve 218 individually. In one embodiment, there are six valves present in the system. The valves are operated in conjunction with movements of the plungers 206 to draw or expel fluids from chamber 202.

In one embodiment, motors 216 are stepper motors which each comprise a motor controller and an actuator. The two plungers 206 are respectively moved by actuators 518 and 528. Actuators 518 and 528 are respectively controlled by controllers 516 and 530. Controllers 516 and 530 are respectively coupled to control module 502 by SERIAL BUS A and SERIAL BUS B, whereby control module 502 specifies desired position, acceleration, and maximum velocity parameters of plungers 206 to controllers 516 and 518.

Control module 502 may further be coupled to receive PRESSURE A and PRESSURE B signals from pressure transducers 520 and 526, respectively, and TEMPERATURE A and TEMPERATURE B signals from temperature sensors 522 and 524. These transducers and sensors are located in corresponding regions of chamber 202 to provide feedback to module 502 and useful observation parameters to the user.

Control module 502 may be configured to provide precision feedback control of plunger movement, fluid flow, and electric fields, based on the current, voltage, temperature, and pressure feedback signals. The microencapsulation and electrostatic coating process steps are preferably carefully controlled to optimize the production of microcapsules.

FIGS. 6–26 are schematic diagrams illustrating the step sequences which may be executed by the microcapsule formation device. Although the reservoirs on each side appear to share a common side inlet/outlet port, this is for illustrative convenience only, and is not intended to suggest a preferred device configuration. Initially, chamber 202 is empty, except for whatever incidental small amount of fluid is left from de-bubbling the device. Reservoirs A and D preferably hold the two immiscible fluids which will form the microcapsules. Reservoir B preferably holds a wash or electrophoretic separation fluid, reservoir F preferably holds a coating and/or storage fluid, reservoir C is preferably designated as a harvesting reservoir, and reservoir E is preferably designated as a waste reservoir. Each reservoir has a corresponding valve which is hereafter referred to by the letter of the corresponding reservoir, i.e. reservoir A is accessible via valve A. In the following description, each valve is assumed to be closed unless otherwise stated. In one embodiment, the dimensions of the chamber are between 1 and 3 inches in diameter and the maximum separation between the plungers during processing is less than 4 inches. In the presence of gravity, the chamber 202 is preferably oriented vertically, and the terms upper and upward refer to the direction opposite the acceleration of gravity. Similarly, the terms lower and downward refer to the same direction as the acceleration of gravity.

One sequence of steps for microcapsule formation is shown in FIGS. 6–10. FIG. 6 shows the filling of the upper chamber with fluid from reservoir A. This is achieved by upward motion of the upper plunger while valve A is opened.

FIG. 7 shows the filling of the lower chamber with fluid from reservoir D. This is achieved by downward motion of the lower plunger while valve D is opened. As fluid from reservoir D is introduced, an interface between the immiscible fluids forms at the filter. The fill takes place slowly so as to avoid undue agitation of the interface. Stepper motors are desirable as actuators for the plungers since they provide very precise control of the plunger's position at low speed and may therefore move the fluid interface away from the filter with minimal disturbance.

FIG. 8 shows the moving of the immiscible fluid interface away from the filter by synchronous upward motion of the two plungers. This is done slowly to avoid applying unduly high fluid shear at the interface. Spontaneous formation of microcapsules may occur at this point for some formulations.

FIG. 9 shows the introduction of controlled fluid shear at the fluid interface by downward motion of the lower plunger while valve A is opened. Alternatively, the fluid shear at the interface may be introduced by upward motion of the upper plunger while valve A is opened. Both methods create a gentle fluid flow along the interface which assists the fluids in "rolling up" to form microcapsules, i.e. the fluid shear caused by the fluid flow counteracts the density stratification effects of gravity and allows surface tension and interfacial coacervation forces to act and cause microdroplets of one fluid to form in the other fluid. Lower fluid shears are preferred, as this generally results in larger capsules of more uniform size, and in one embodiment, the fluid shear is strictly limited to less than 100 dynes/cm$^2$. In cases where the densities and viscosities of the two fluids are comparable, the fluid shear may be limited to less than 50 dynes/cm$^2$. Typically the fluid shear is limited to less than about 20 dynes/cm$^2$, and for the formation of large microcapsules, fluid shears of about 12 dynes/cm$^2$ or less are preferable.

FIG. 10 shows the first emptying of the lower chamber into waste reservoir E. This is achieved by upward motion of the lower plunger while valve E is opened.

FIGS. 11–14 show a sequence of steps which may be used to wash the microcapsules. This sequence may follow the formation sequence and the coating sequence (described further below). FIG. 11 shows the transfer of fluid from the upper chamber to the lower chamber by synchronous downward movement of both plungers. Microcapsules larger than the pore size of the filter membrane are collected on the filter.

FIG. 12 shows a second emptying of the lower chamber into waste reservoir E. This is achieved by upward motion of the lower plunger while valve E is opened.

FIG. 13 shows the filling of the upper chamber with fluid from reservoir B. This is achieved by upward motion of the upper plunger while valve B is opened. This operation may re-suspend the microcapsules in a rinse solution.

FIG. 14 shows the emptying of the upper chamber into waste reservoir E by downward motion of the upper plunger while valve E is opened. This operation may be used to rinse the microcapsules collected on the filter.

FIGS. 15–16 show a sequence of steps which may be used to re-suspend microcapsules which have been collected on the filter. This sequence typically follows a wash sequence. FIG. 15 shows the filling of the lower chamber with a suspension fluid from reservoir F. This is achieved by downward motion of the lower plunger while valve F is opened. The suspension fluid could be a storage fluid or a coating fluid, or a fluid which serves as both.

FIG. 16 shows the transfer of fluid from the lower chamber to the upper chamber by synchronous upward motion of the plungers. This operation lifts the microcapsules from the filter and suspends them in the coating or suspension fluid. In one embodiment, the plungers are moved to positions equidistant from the filter.

FIG. 17 shows an optional electrostatic coating step, in which an electric field is imposed between the plungers. This operation is performed for electrostatic coating of the microcapsules when the microcapsules are suspended in a coating fluid. In one embodiment, the voltage is raised in steps to a desired maximum electric field strength of up to 500 V/cm (typically with currents of less than 25 mA) and held for around 1 to 15 minutes while the coating material deposits onto the surfaces of the microcapsules.

FIGS. 18–19 show an optional sequence of steps for free-zone electrophoretic separation. This sequence follows a wash sequence. FIG. 18 shows the filling of the upper chamber with a low conductivity buffer solution by upward motion of the upper plunger while valve B is opened. This is done slowly to avoid agitating the collected microcapsules off the filter and distributing them throughout the upper chamber.

FIG. 19 shows the imposition of an electric field between the plungers. The microcapsules will typically have various surface charge densities, and the microcapsules with the highest surface charge densities will move faster than microcapsules which have lower surface charge densities. Accordingly, the microcapsules will segregate themselves into layers, each layer moving at a velocity indicative of the surface charge density of its members. Members of certain layers may be more desirable due to their surface charge densities (e.g. microcapsules from one layer may more preferentially target certain tissues), and these layers may be harvested exclusive of other layers. Variations on the electrophoresis technique may also be conducted in this manner, including density-gradient electrophoresis and density-gradient electrophoresis with iso-electric focussing FIGS. 20–21 show a sequence of steps which may be used for harvesting microcapsules. This sequence may immediately follow a suspension sequence, a coating operation, or an electrophoretic separation sequence. FIG. 20 shows the emptying of the lower chamber into waste reservoir E by upward motion of the lower plunger while valve E is opened. This operation acts to remove unnecessary fluid from the lower chamber.

FIG. 21 shows the emptying of the upper chamber into harvesting reservoir C by downward motion of the upper plunger while valve C is opened. The completed microcapsules are thereby collected in reservoir C and thus the microencapsulation and electrostatic coating process is completed. For harvesting operations after electrophoretic separation, the harvesting would typically take place through outlet ports in the plunger, and an additional waste reservoir would be used for the undesired microcapsule layers. The plunger outlet ports may be preferably located between about 1/7 and 1/5 diameter inward from the outer edge of the plunger, as this is where fluid flow induced by the electrophoretic separation process is balanced.

FIGS. 22–26 are schematic diagrams illustrating an alternate sequence of steps which may be executed by the microcapsule formation device in an inverted orientation. Initially, chamber 202 is empty, except for whatever incidental small amount of fluid is left from de-bubbling the device. The reservoirs contain the same fluids as in FIG. 6, but the device is now inverted, i.e. the upper chamber and upper plunger are now the lower chamber and lower plunger, and vice versa.

FIG. 22 shows the filling of the lower chamber with fluid from reservoir A by downward motion of the lower plunger while valve A is opened. FIG. 23 shows the filling of the upper chamber with fluid from reservoir D by upward motion of the upper plunger while valve D is opened. In this sequence, the density of the fluid from reservoir D is assumed to be greater than the density of the fluid from reservoir A, and the reason for the inversion of the device is to produce a fluid density inversion at the interface, i.e. the fluid above the interface is denser than the fluid below the interface.

FIG. 24 shows the moving of the immiscible fluid interface downward away from the filter by slow synchronous downward motion of the plungers. Although the interface is somewhat unstable due to the density inversion, this instability assists in the formation of microcapsules as long as the interface can be maintained, as shown in FIG. 25. The remaining processing steps are conducted similarly to those of the previous sequence, starting with FIG. 10, and replacing the terms "upper" and "upward" with "lower" and "downward", and vice versa.

The preferred embodiments of the present invention have been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, rather than microprocessor controlled operation of the plungers and valves, manual operation may be used. The membrane may be movable within the chamber, so that separation from the interface is achieved by moving the filter rather than the interface. The device may be used with microcapsule-formation fluids which are not technically immiscible, but which nevertheless form a meniscus-like interface. All such modifications are intended to be included within the scope of the appended claims.

What is claimed is:

1. A microencapsulation device which comprises:
   a chamber having a first and second region along a length of the chamber, wherein;
   a filter situated substantially perpendicular to the chamber length, wherein the first region is below and adjacent to the filter and the second region is above and adjacent to the filter, the filter having a maximum pore size of between 1 and 100 microns;
   a first inlet port in fluid communication with the first region, wherein a first fluid is introduced into the first region below the filter;
   a second inlet port in fluid communication with the second region wherein a second fluid is introduced into the second region, wherein the second fluid is immiscible with the first fluid, whereby a quiescent interface between the first and second fluids is formed at the filter;
   an auxiliary port in communication with the first or second region, wherein fluid is introduced into or withdrawn from the first or second region;
   a first plunger slidably movable along the length of the chamber below the filter, wherein when the first plunger is moved toward the second region the quiescent interface moves upward into the second region away from the filter while maintaining fluid shear forces at the interface of less than 100 dynes/cm$^2$, said interface is formed between an aqueous solution and a hydrocarbon solution having a dissolved membrane-forming substance therein, said membrane-forming substance being substantially insoluble in water, whereby surface tension and interfacial coacervation at the interface cause formation of liquid microcapsules surrounded by a membrane;
   a second plunger slidably movable along the length of the chamber above the filter, wherein the movement of the second plunger moves fluid in the direction of movement of the second plunger, such that when the second plunger is moved toward the first region fluid will move from the second region through the filter into the first region; and
   a first electrode and a second electrode situated on opposing ends of the first or second region to provide an electric field across the second region, whereby microcapsules suspended in the coating fluid are electrostatically coated.

2. A microencapsulation device for interacting two immiscible fluids to make microcapsules, said device comprising:
   a chamber having a first and second region;
   a first inlet port in fluid communication with the first region, wherein a first fluid is introduced into the first region;
   a second inlet port in fluid communication with the second region, wherein a second fluid is introduced into the second region;
   a filter dividing the first and second region, wherein the filter has one surface in contact with the first fluid and a second surface in contact with the second fluid, the filter being porous to allow the interaction of the first and second fluid;
   a first plunger, wherein a face of the first plunger defines one end of the first region, said first plunger is slidably moveable in the chamber, whereby the movement of said first plunger adjusts the volume of the first region; and a first electrode and a second electrode situated on opposing ends of the first or second region such that when an electric field is applied across the first or second region charged particles in the region where the electric field is applied will undergo electrophoretic migration according to the surface charge density of the particles.

3. A microencapsulation device for interacting two immiscible fluids to make microcapsules, said device comprising:

a chamber having a first and second region;

a first inlet port in fluid communication with the first region, wherein a first fluid is introduced into the first region;

a second inlet port in fluid communication with the second region, wherein a second fluid is introduced into the second region;

a filter dividing the first and second region, wherein the filter has one surface in contact with the first fluid and a second surface in contact with the second fluid, the filter being porous to allow the interaction of the first and second fluid;

a first plunger, wherein a face of the first plunger defines one end of the first region, said first plunger is slidably moveable in the chamber, whereby the movement of said first plunger adjusts the volume of the first region;

a coating inlet port traversing the first plunger wherein a coating fluid is introduced into the first region, wherein movement of the first plunger towards the second region moves the coating fluid from the first region through the filter into the second region; and a first electrode and a second electrode situated on opposing ends of the first or second region such that an electric field is applied across the first or second region.

4. An apparatus for making microcapsules, wherein the device comprises:

a chamber having a first region for holding a first fluid and a second region for holding a second fluid;

wherein a volume of fluid in the first region is adjustable;

a first inlet port in fluid communication with the first region;

wherein said second fluid is immiscible with the first fluid and forms an interface with the first fluid;

a second inlet port in fluid communication with the second region;

a plunger, wherein a face of the plunger defines one end of the first region, wherein said plunger is slidably moveable in the chamber, the movement of said plunger adjusts the volume of the first region;

a porous membrane configurable to stabilize the interface between the first and second fluids, wherein the porous membrane divides the first and second region and assists in minimizing fluid shear at the interface; and a first electrode and a second electrode configurable to provide an electric field across the second region, thereby electrostatically coating microcapsules suspended in the second region.

5. An apparatus for making microcapsules, wherein the device comprises:

a chamber having a first region for holding a first fluid and a second region for holding a second fluid;

wherein a volume of fluid in the first region is adjustable;

a first inlet port in fluid communication with the first region;

wherein said second fluid is immiscible with the first fluid and forms an interface with the first fluid;

a second inlet port in fluid communication with the second region;

a first plunger, wherein a face of the first plunger defines one end of the first region, wherein said first plunger is slidably moveable in the chamber, the movement of said first plunger adjusts the volume of the first region;

a second plunger, wherein a face of the second plunger defines one end of the second region, wherein said second plunger is slidably moveable in the chamber, the movement of said second plunger adjusts the volume of the second region;

a porous membrane configurable to stabilize the interface between the first and second fluids, wherein the porous membrane divides the first and second region and assists in minimizing fluid shear at the interface; and a controller programmed to sequentially perform a sequence of operations to create microcapsules, wherein the sequence includes:

increasing the first region volume to draw the first fluid into the first region through the first inlet port;

increasing the second region volume to draw the second fluid into the second region through the second inlet port; and synchronizing the movement of the first and second plungers to move the fluid interface away from the porous membrane into the second region.

6. An apparatus for making microcapsules, wherein the device comprises:

a chamber having a first region for holding a first fluid and a second region for holding a second fluid;

wherein a volume of fluid in the first region is adjustable;

a first inlet port in fluid communication with the first region;

a second region for holding a second fluid, wherein said second fluid is immiscible with the first fluid and forms an interface with the first fluid;

a second inlet port in fluid communication with the second region;

a first plunger, wherein a face of the first plunger defines one end of the first region, wherein said first plunger is slidably moveable in the chamber, the movement of said first plunger adjusts the volume of the first region;

a second plunger, wherein a face of the second plunger defines one end of the second region, wherein said second plunger is slidably moveable in the chamber, the movement of said second plunger adjusts the volume of the second region;

a porous membrane configurable to stabilize the interface between the first and second fluids, wherein the porous membrane divides the first and second region and assists in minimizing fluid shear at the interface; and first and second electrodes situated on opposing ends of the first and second region.

* * * * *